United States Patent
Fry et al.

(10) Patent No.: US 6,251,966 B1
(45) Date of Patent: Jun. 26, 2001

(54) DENTAL ADHESIVE AND USE THEREOF IN PREPARING DENTAL IMPRESSION

(75) Inventors: Bryan E. Fry, Tecumseh; Eugene R. Martin, Onsted, both of MI (US)

(73) Assignee: Wacker Silicones Corporation, Adrian, MI (US)

( * ) Notice: Subject to any disclaimer, the term of this patent is extended or adjusted under 35 U.S.C. 154(b) by 0 days.

(21) Appl. No.: 09/263,996

(22) Filed: Mar. 5, 1999

(51) Int. Cl.[7] ............................. A61K 6/10; C08L 83/04
(52) U.S. Cl. ..................... 523/109; 523/120; 106/35; 524/588; 524/858; 524/860; 524/861; 524/862; 525/474; 525/477; 525/478
(58) Field of Search ........................... 523/109, 120; 106/35; 524/858, 860, 861, 862, 588; 525/474, 477, 478

(56) References Cited

U.S. PATENT DOCUMENTS

| | | |
|---|---|---|
| 4,613,534 * | 9/1986 | Blizzard et al. ................ 428/57 |
| 4,763,791 | 8/1988 | Halverson et al. . |
| 4,923,400 | 5/1990 | Suzuki et al. . |
| 5,108,286 | 4/1992 | Freedman et al. . |
| 5,190,827 * | 3/1993 | Lin ............................. 428/447 |
| 5,302,630 | 4/1994 | Mukai et al. . |
| 5,576,110 * | 11/1996 | Lin et al. ..................... 428/447 |
| 5,580,915 * | 12/1996 | Lin ............................. 524/267 |
| 5,602,214 * | 2/1997 | Lin et al. ..................... 525/478 |

* cited by examiner

*Primary Examiner*—Robert Dawson
*Assistant Examiner*—Jeffrey B. Robertson
(74) *Attorney, Agent, or Firm*—Brooks & Kushman P.C.

(57) ABSTRACT

An organopolysiloxane adhesive contains an organopolysiloxane rubber base, an organopolysiloxane pressure sensitive adhesive, a aliphatic unsaturated-functional M'Q resin, and a polyhydrido-functional organopolysiloxane in an organic solvent, and exhibits differential adhesion between dental impression material and dental impression tray material.

20 Claims, No Drawings

DENTAL ADHESIVE AND USE THEREOF IN PREPARING DENTAL IMPRESSION

TECHNICAL FIELD

The present invention pertains to dental adhesives and to processes for preparing dental impressions using these adhesives.

BACKGROUND ART

Adhesives used in dental work are subject to exacting physical property requirements. At the same time, such adhesives, due to the likelihood of contact with the gums and other tissue, must employ non-toxic and non-irritating components.

In restorative dentistry, for example the preparation of crowns, bridges, and dentures, a casting operation is used which requires a reasonable degree of accuracy in recreating the natural contours of teeth and gums. For such purposes, a female casting, or "impression" is made in the mouth, using a curable dental "impression" material.

In preparing such impressions, an impression tray is used. This impression tray is a U-shaped trough which fits over the teeth and gums, and which may be made of plastic, metal or other materials. A curable polymer impression material is placed in the tray, and the tray pushed down (or up) onto the teeth and gums. Following cure, the tray and cured impression material is removed.

The impression material itself must be non-toxic and non-irritating, and must rapidly cure without the generation of excessive heat. The impression material must also exhibit low shrinkage in order to retain accuracy, and must be elastomeric in order that it may be removed from the teeth and gums without destroying the mold thus produced.

Because of these relatively stringent requirements, two component addition-curable, room temperature vulcanizable (RTV-2) organopolysiloxane elastomers are widely used as dental impression materials. These curable systems generally include hydrogen-functional organopolysiloxanes and unsaturated organopolysiloxanes, with a platinum hydrosilylation catalyst contained in one component. The two components are mixed just prior to use, and cure rapidly. However, in order to remove the cast impression from the oral cavity, it is necessary for the impression material to exhibit greater adhesion to the dental tray than to the teeth and gums. In general, impression materials have insufficient adhesion for this purpose, and thus a dental adhesive is used between the tray and impression material. However, the nature of the impression tray surface on the one hand, and the impression material on the other hand, makes formulation of an adhesive which can suitably adhere to both tray and impression material difficult.

In U.S. Pat. No. 4,763,791, which may be referred to for background information, a kit is disclosed which contains dental trays as well as impression material and dental adhesive. However, the identity of the adhesive and its composition is not disclosed. U.S. Pat. No. 5,108,286 attests to the difficulties encountered due to the stringent requirements for adhesion of impression material to mouth tissues and the impression tray. Rather than employ a separately applied adhesive, the '286 inventors chose instead to employ a special bi-adhesive laminate, containing a high strength innermost plastic film coated on both surfaces with an adhesive layer. Removable foils are employed to keep the adhesives fresh. A benefit of the '286 process is that two different adhesives may be used, one tailored for adhesion to the impression tray, and one tailored for adhesion to the impression material. However, the use of such products is cumbersome and requires some dexterity in conforming the adhesive laminate to the impression tray.

It would be desirable to provide a dental adhesive which is formulated to have the requisite adhesion to both the impression tray and to the impression material without requiring two separate adhesive compositions, or the use of adhesive laminates. It would be further desirable to provide such an adhesive in a liquid form which can be brushed or sprayed onto the impression tray. It would be further desirable to provide an adhesive which can be applied to an impression tray several hours before use without relinquishing its desirable adhesive properties.

DISCLOSURE OF INVENTION

It has now been surprisingly discovered that an organopolysiloxane adhesive composition, containing an organopolysiloxane rubber, an organopolysiloxane pressure-sensitive adhesive, a hydrogen-functional organopolysiloxane, and an unsaturated organopolysiloxane resin, can simultaneously provide the differing adhesive requirements for tray adhesion and impression material adhesion. The dental adhesives of the subject invention, when dissolved in organic solvent, are liquids of relatively low viscosity which rapidly dry so that they may be used directly after application, yet retain their ability to adhere to impression material for a considerable length of time after drying. The dental adhesives may also be used for other applications where a tenacious bond between materials with differing surface properties is required, for example in dentures between the denture and an elastomeric pad.

DESCRIPTION OF PREFERRED EMBODIMENTS

The dental adhesives of the subject invention are one-part organopolysiloxane compositions whose organopolysiloxane solids are dissolved in organic solvent. The organopolysiloxanes present in the composition are an organopolysiloxane rubber base, a pressure-sensitive organopolysiloxane adhesive base, a polyhydrido-functional organopolysiloxane crosslinker, and an unsaturated organopolysiloxane resin.

The organopolysiloxane rubber base is a high molecular weight organopolysiloxane rubber or gum, preferably an unsaturated organopolysiloxane rubber, and more preferably a vinyl-functional organopolysiloxane rubber. The terms "rubber" and "gum" are used herein interchangeably. Such rubbers in general, are composed predominately of $$R_a R^1_b SiO_{\frac{4-a-b}{2}} \quad (I)$$

moieties where R is an alkyl, cycloalkyl, aryl, aralkyl, or alkaryl group of less than 30 carbon atoms, preferably a $C_{1-18}$ alkyl group, and most preferably a methyl group; and $R^1$ is an unsaturated organic group, preferably an alkenyl group, alkenyl ether group, acrylate or methacrylate group, or the like, more preferably a $C_2$–$C_6$ terminally unsaturated alkenyl group, and most preferably a vinyl group; a and b are integers of from 0 to 2, and the sum of a and b is 2.

The rubber component also generally includes terminal groups of the formula $$X_c R_d R^1_e SiO_{\frac{4-c-d-e}{2}} \quad (II)$$

wherein X may be $C_{1-8}$ alkoxy or hydroxy, R and $R^1$ have the meanings above, and c, d, and e are integers of from 0 to 3, and the sum c+d+e=3. The rubber component may also include minor amounts of moieties.

$$R_f R^1_g SiO_{\frac{4-f-g}{2}} \quad (III)$$

and $$\frac{SiO_4}{2} \quad (IV)$$

where R and $R^1$ have the above meanings, f and g are integers of 0 or 1, and the sum of f+g is 1. The total of units III (T units) and IV (Q units) must be such that the organopolysiloxane is still elastomeric, and capable of solution in the organic solvent and other system components. Preferably, the amounts of III and IV moieties in the organopolysiloxane gum or rubber is less than 10 mol percent. Most preferably, the organopolysiloxane gum or rubber is a methylvinyl organopolysiloxane obtainable from Wacker-Chemie GmbH and Wacker Silicones Corporation as ELASTOSIL® rubber base, e.g. ELASTOSIL® R401/40, R401/50, R401/60, R401/70, R401/80, and R401/90 rubber bases, most preferably ELASTOSIL® R401/70 rubber base.

The rubber base is preferably employed in an amount of 2 weight percent to about 20 weight percent, more preferably 6 weight percent to about 10 weight percent, and most preferably about 7–8 weight percent, these weight percents based on total organopolysiloxane solids in the dental adhesive. These amounts assume that the gum or rubber contains approximately 29% fumed silica or other filler. When calculated without the filler, the amount of gum in the formulation is accordingly less.

The pressure-sensitive adhesive base is, in general, an organopolysiloxane composition which displays pressure-sensitive or tacky adhesive characteristics following drying from solution in organic solvent. Most preferably, the pressure-sensitive adhesive base will be the product obtained by heating together a silanol-terminated organosiloxane fluid containing terminal groups II where X is OH, R is preferably methyl, d=2, and e is 0, and non-terminal groups I where a is 2 and R is methyl, optionally containing D units having both methyl and hydroxy-functionality; with an MQ resin containing methyl, silanol, and substituents, the reaction taking place in the presence of organic solvent, preferably an aliphatic solvent such as Isopar®G petroleum solvent available from Exxon. Preferably, the MQ resins are copolymers obtained from the reaction of tetralkylsilicates and a lower siloxane, for example hexamethyldisiloxane. A preferred MQ resin for preparation of the pressure-sensitive adhesive base is MQ 803 resin available from Wacker Chemie. MQ resins generally contain traces of toluene due to their method of preparation, and while not shown, may contain other groups incident to their preparation as well, e.g. chloro groups and lower alkoxy groups, by way of example, and not limitation. A preferred silanol-functional organopolysiloxane is Polymer N3C, available from Wacker-Chemie GmbH. The MQ resin and silanol-functional organopolysiloxane are reacted at elevated temperatures at or less than the boiling point of the mixture, generally in the presence of a tertiary ammonium hydroxide base, at MQ resin to silanol-functional organopolysiloxane ratios of 1:2 to about 2:1. A pressure-sensitive adhesive base which is fully prepared is available from Wacker-Chemie as PSA 45525 VP, which contains 50% solids, the balance being organic solvent. The amount of pressure-sensitive adhesive, in terms of pressure-sensitive adhesive solids to total organopolysiloxane solids, is about 10% to 25%, preferably 16% to 22%, and most preferably 16% to 17%. As a 50% solids solution, these percentages are doubled, relative to total organopolysiloxane solids.

The polyhydrido-functional organopolysiloxane is a fluid organopolysiloxane containing moieties bearing both alkyl groups and silicon-bonded hydrogen, either in terminal groups or in D groups, in the latter case thus having silicon-bonded hydrogen dispersed along the polymer chain. The predominant moieties are thus both terminal moieties:

$$H_h R_i R^1_j SiO_{\frac{4-h-i-j}{2}}$$

where h is an integer from 0 to 2, i is an integer from 1 to 3, and j is an integer from 0 to 3; R and $R^1$ have the meanings given previously; and the sum h+i+j=3, wherein h is preferably 1; i is preferably 2; and j is preferably 0; and non-terminal units:

$$H_k R_l R^1_m SiO_{\frac{4-k-l-m}{2}}$$

wherein k is 0, 1, or 2 but is preferably 0 or 1; l is 0, 1, or 2 but is preferably 1 or 2; and m is 0, 1, or 2 but is preferably 0. Thus, the polyhydrido organopolysiloxanes may contain unsaturated functionality, e.g. vinyl functionality, in addition to hydrido functionality. Most preferably the polyhydrido organopolysiloxanes are substantially linear organopolysiloxanes containing dimethylsiloxy and methylhydrogensiloxy repeating units, with trimethylsiloxy and/or dimethylhydrogensiloxy termination. The polyhydrido organopolysiloxane fluids generally contain from 0.05 weight percent to about 3 weight percent Si—H hydrogen, more preferably 0.1 weight percent to 1 weight percent.

The polyhydrido organopolysiloxane is preferably employed, in weight percent relative to total organopolysiloxane weight percent, in amounts of 1% to 20%, more preferably 2% to 10%, and most preferably 2% to 6%. These weight percentages are calculated based on Si—H bound hydrogen content of 0.5 weight percent. If crosslinkers having lower or higher hydrido content are used, these amounts should be adjusted accordingly.

The unsaturated organopolysiloxane resin may be characterized generally as an M'Q resin, where M' may be either an M group or $M_{vinyl}$ group. This resin may also contain D and T units in addition to the predominant M and Q units. Resins such as these are relatively high molecular weight, highly branched molecules which are solids at room temperature and generally soluble in organic solvents. The resins are prepared by reacting organosilicates with a di- or polysiloxane, generally in an organic solvent such as xylene or toluene, although aromatic solvent-free preparations are also known. At least a portion of the di- or polysiloxane, more preferably di- or oligosiloxane, will contain alkyl groups and alkenyl or alkynyl groups, such as sym-dimethyltetravinyldisiloxane, sym-tetramethyldivinylsiloxane, and the like. Terminally unsaturated alkenyl radicals are preferred, vinyl radicals beings most preferred.

The M'Q resins are designated as such herein to indicate that these resins contain reactive unsaturation, preferably vinyl groups or other reactive unsaturated groups such as vinylether, acrylate, propenyl, allyl, hexenyl, etc. However, the resins also contain moieties without unsaturation, i.e. should not be construed as "homopolymeric". Preferred M units are trimethylsilyl, vinyldimethylsilyl, ω-hexenyldimethylsilyl, and the like. In general, the M'Q resins contain from about 0.1 weight percent to about 10 weight percent, more preferably, 0.5 weight percent to 3 weight percent unsaturated functionality. A preferred M'Q resin is MQ 804 resin available from Wacker Chemie. The unsaturated M'Q resin is used in amounts, in weight percent based on total weight of organopolysiloxane solids, of 30% to 80% more preferably 40% to 70%, and most preferably 50% to 60%. Based on the above, it can be seen that M'Q resins are a subset of MQ resins.

The dental adhesive also contains considerable organic solvent, preferably from 30 weight percent to 70 weight percent, more preferably 40 weight percent to 60 weight percent, and most preferably 45 to 55 weight percent, these amounts not inclusive of any solvents supplied along with the pressure sensitive adhesive base or the unsaturated M'Q resin in customary amounts. When these amounts are considered also, total solvent is correspondingly higher then the percentages previously given.

In the dental adhesives of the present invention, the weight percentages of the four organopolysiloxane components (A) through (D), as previously stated, are calculated relative to the total organopolysiloxane content, i.e. the sum of components (A) through (D), and thus the sum of these percentages must total 100%.

In addition to the foregoing, the adhesive may contain viscosity adjusting agents, rheology control agents, catalysts, pigments, flavorants, odor oils, and fillers. The weight percent of solids used herein and in the claims are based on compositions employing rubbers or gums containing about 28 weight percent filler, preferably fumed silica. By the term "solids" in this context is meant solids supplied as one of the four necessary components. If the filler is omitted from the rubber, or included in another component in whole or in part, the weight percentages should be adjusted accordingly. Additional filler may be added to the formulation as desired for purposes of increasing its viscosity. Particularly useful are fillers or other additives which impart non-Newtonian character to the adhesive, i.e., a viscosity which is inversely proportional to shear rate, allowing the adhesive to be readily brushed or sprayed onto a substrate, but exhibiting little running, sagging, or dripping.

The subject invention adhesives may be prepared by admixing the ingredients in any order which allows for the preparation of a homogenous adhesive composition. The adhesive compositions are preferably substantially particle-free. By "particle-free" is meant that there are no substantial amount of purposefully added particles which are observable to the eye, generally no particles whose size exceeds about 10 $\mu$m, and preferably containing substantially no particles of particle size greater than 2 $\mu$m. Most preferably, any particulates will be below 1 $\mu$m in size. In general, the rubber base may be first divided into small "chunks" so as to allow for dissolution in the solvent over a reasonable length of time. The dissolving of the rubber base and further processing is preferably conducted under a nitrogen or other relatively inert gas atmosphere. Following solution of the rubber base, the remaining siloxanes are added, preferably in the order of M'Q resin powder, pressure-sensitive adhesive, and crosslinker. However, if desired, all materials can be mixed and dissolved at the same time.

The composition is well blended, for example, in a Myers mixer or similar device, for a period sufficient to provide a homogenous product, generally in excess of one hour, and preferably about 4 hours. The viscosity of the product, measured on a Brookfield viscosimeter using an RTV Spindle #3 and a rotational speed of 50 sec$^{-1}$ is preferably between 50 cP and 300 cP, more preferably between 100 cP and 200 cP, and most preferably about 140 cP. Lower viscosities can be tolerated if considerably non-Newtonian behavior is exhibited. For example, an adhesive which exhibits a viscosity of only 10 cPs at 50 sec$^{-1}$ but 1000 cP at 1 sec$^{-1}$ would be quite suitable. It is preferable that the final product be filtered, for example through a 150 mesh filter, to remove any large particulates which may have formed or which may have been introduced from other sources. If flavorants, perfumes, fillers, catalysts, and the like are added, these are preferably added toward the end of the mixing cycle. Solvents may also be added to adjust viscosity, or to adjust the solids content, which preferably is between 30 weight percent and 70 weight percent, more preferably between 35 and 50 weight percent, and most preferably about 40 weight percent.

The dental adhesive solution may be applied by brushing, spraying, dipping, or any other suitable application method. The substrate may be metal or plastic, but is preferably a plastic dental tray or dental tray insert. The adhesive is allowed to dry, and may be used immediately after drying or within 1–2 hours to several days, depending upon the particular formulation. Trays having fresh adhesive applied which are stored in the cold may have a longer life prior to becoming ineffective. Most preferably, the adhesives have useful, pre-casting service lives of from about 4 hours to 6 hours. Thus, the dental adhesives may be applied immediately prior to use, or may be prepared several hours earlier. This is especially useful in dentists' offices, where a technician may make the required number of trays for the day's work in the early morning, or in the morning and at noon, thus saving waiting time which would otherwise occur if the trays were prepared just prior to use.

Once the adhesive is dry, it is generally tack free. Drying takes but a few minutes. The service life can be extended, if desired, by refrigeration of the adhesive-coated trays. In use, the curable impression material, which is preferably a two-part curable silicone elastomer resin containing, after mixing, both unsaturated-functional groups and Si—H bound hydrogen, and a hydrosilylation curing catalyst, is introduced into the dental impression tray and the tray placed over the patients teeth and gums and allowed to cure. The dental adhesive allows molding in inverted position without the impression material falling out of the tray. Following cure, the tray and female impression are worked loose from the teeth. The cured impression material remains bonded to the liner or tray during subsequent casting steps.

In the case of impression materials which cure by hydrosilylation in the presence of a hydrosilylation catalyst, it is believed that the catalyst present in the impression material also causes partial or full cure of the adhesive. Thus, no catalyst is necessary in the dental adhesive when such catalysts are present in the casting material. For other systems, the mode of operation is not well understood. The actual method of cure, or the degree of cure or lack thereof, forms no part of the present invention except as set forth herein.

The dental adhesive can be supplied packaged in many forms, for example tear-open foil packs, cut-off squeeze tubes, metal tubes such as might be used to supply toothpaste, metal cans, and the like. Because of the presence of Si—H containing materials, storage in glass bottles, vials, etc., is not recommended.

Having generally described this invention, a further understanding can be obtained by reference to certain specific examples which are provided herein for purposes of illustration only and are not intended to be limiting unless otherwise specified.

In the following examples, candidate adhesives are prepared and tested by brushing the adhesive onto a plastic dental tray and allowing it to dry for several minutes until a tack-free surface exists. Next, the well-mixed liquid impression elastomer is injected into the tray over the adhesive layer so that the tray is completely full. The filled tray is allowed to cure at room temperature until the impression material has thoroughly solidified. After curing, the bond strength of the adhesive is tested by attempting to separate the elastomer from the tray by pulling with one's fingers. If the elastomer can be pulled from the tray with minimal or no breakage of the impression, the adhesion is considered inadequate. If however, the elastomer cannot be removed from the tray without breaking it or tearing it into several smaller pieces, the adhesion is adequate and the adhesive is considered to be favorable. This behavior may be termed "substantial adhesion" as that term is used herein. Unless otherwise indicated, the various components are all commercial products from Wacker-Silicones, Adrian, Mich.

COMPARATIVE EXAMPLE 1

An adhesive is formulated from 96.59 weight percent of CRA 81, an MQ resin (MQ resin 803) supplied in xylene and available from Wacker Silicones Corp., and 3.41 weight percent Crosslinker 525, a Si—H-functional organopolysiloxane containing approximately a 2:1 ratio of dimethylsiloxy to methylhydrogensiloxy groups, also available from Wacker Silicones. The formulation contains ca. 50 weight percent solids. However, when tested as an adhesive, adhesion between the dental tray and the impression material is found to be inadequate. The cured impression material is too easily removed from the tray.

COMPARATIVE EXAMPLE C2

Analogously to Comparative Example C1, an adhesive was formulated from 89.67 weight percent PSA45525 a pressure sensitive adhesive described previously, and 10.33 weight percent Crosslinker 525. Adhesion was also inadequate.

COMPARATIVE EXAMPLE C3

An adhesive was prepared, containing 6.3 weight percent MQ resin 803, 9.3 weight percent Finish CT (3M), a hydroxyl-terminated organopolysiloxane gum; 70.8 weight percent CRA 81; 2.5 weight percent Crosslinker 525; and 11.1 weight percent Isopar G, a paraffinic solvent available from Exxon Corporation. The adhesive exhibited poorer adhesive then Comparative Examples C1 and C2.

COMPARATIVE EXAMPLE C4

An adhesive was prepared containing 6.3 weight percent MQ resin 803; 4.3 weight percent Finish CT; 5.0 weight percent of Elastosil® R401/70 organopolysiloxane rubber (29% fumed silica content) (Wacker Silicones); 70.8 weight percent CRA 81; 2.5 weight percent crosslinker 525; and 11.1% Isopar G. The adhesion was poor, less than that of Comparative Examples C1 and C2.

EXAMPLE 1

A dental adhesive was prepared by dissolving 5.0 parts Elastosil® R401/70 organopolysiloxane rubber base in 64.3 parts Isopar E under nitrogen. The remaining ingredients were then added: 35.2 parts MQ resin powder 804, an M'Q resin containing vinyl unsaturation; 21.6 parts pressure sensitive adhesive PSA 45525 VP; and 2.5 parts crosslinker 525. The mixture was blended at high speed for 4 hours and tested for viscosity (140 cP), flash point (44° F.), and weight percent solids (42%). The product was then filtered through a 150 mesh bag filter. The adhesive demonstrated excellent adhesion to dental trays and dental impression material.

The above examples illustrate the difficulties encountered with formulating a suitable dental adhesive. Of the adhesives tested, only the subject invention adhesive displays the necessary degree of adhesion between both tray and impression material to function satisfactorily as dental adhesive. The dental adhesives of the subject invention, while formulated with a particular end use in mind, can also be used in other applications where tailored and generally differential adhesion requirements between differing substrates is required, both in the dental area and the non-dental area. In the dental area, for example, the subject adhesives can be cured as a primer between reworked dentures and soft reline material.

In the specification and claims herein, all materials may be used to the exclusion of other named or unnamed materials, with the exception of at least one ingredient from the four necessary classes of ingredients (A) through (E). It should be noted that some components may be supplied in or with other components, i.e., a crosslinker may be supplied dissolved in paraffinic solvent, thus supplying a portion of the latter. The terms "a: and "an" mean one or more unless otherwise indicated, or unless the context clearly indicates otherwise.

While embodiments of the invention have been illustrated and described, it is not intended that these embodiments illustrate and describe all possible forms of the invention. Rather, the words used in the specification are words of description rather than limitation, and various changes may be made without departing from the spirit and scope of the invention.

What is claimed is:

1. An organopolysiloxane adhesive composition, comprising, in weight percent based on the total weight of component (A) through (D) of the composition:
   (A) from about 2% to about 20% of at least one organopolysiloxane rubber base;
   (B) from about 10% to about 25% of at least one organopolysiloxane pressure sensitive adhesive;
   (C) from about 30% to about 80% of at least one aliphatic unsaturation-functional organopolysiloxane M'Q resin;
   (D) from about 1% to about 20% of at least one Si—H functional organopolysiloxane crosslinking agent containing minimally 3 Si—H bound hydrogens per molecule on average;
   components (A) through (D) dissolved in
   (E) sufficient organic solvent to obtain a solids content of ingredients (A) to (D) of from 30 percent to about 70% based on the total weight of the adhesive,
   wherein the sum of the weight percentages of components A to D is 100% based on the weight of components A to D, and wherein following evaporation of solvent, a non-tacky film is formed.

2. The adhesive composition of claim 1, wherein said organopolysiloxane rubber is a vinyl-functional organopolysiloxane rubber, and said M'Q resin (C) is a vinyl-functional MQ resin.

3. The adhesive composition of claim 1, containing the components (A)–(D) in amounts of:

(A) 6%–10%

(B) 16%–22%

(C) 40%–70%

(D) 2%–10%.

4. The adhesive of claim 3 wherein said organic solvent is present in an amount of from 45–55 weight percent based on the sum of components (A) through (E).

5. The adhesive of claim 1 wherein said organic solvent comprises an aliphatic hydrocarbon solvent.

6. The adhesive of claim 1 wherein said adhesive is free of fillers having a mean particle size in excess of 10 μm.

7. An organopolysiloxane adhesive composition, comprising, in weight percent based on the total weight of component (A) through (D) of the composition:
(A) from about 2% to about 20% of at least one organopolysiloxane rubber base;
(B) from about 10% to about 25% of at least one organopolysiloxane pressure sensitive adhesive;
(C) from about 30% to about 80% of at least one aliphatic unsaturation-functional organopolysiloxane M'Q resin;
(D) from about 1% to about 20% of at least one Si—H functional organopolysiloxane crosslinking agent containing minimally 3 Si—H bound hydrogens per molecule on average;
components (A) through (D) dissolved in
(E) sufficient organic solvent to obtain a solids content of ingredients (A) to (D) of from 30 percent to about 70% based on the total weight of the adhesive;
wherein said adhesive exhibits substantial adhesion to both a curable organopolysiloxane dental impression material and a dental impression tray, and wherein the sum of the weight percentages of components A to D is 100% based on the weight of components A to D.

8. The adhesive of claim 7 which exhibits substantial adhesion to subsequently added dental impression material for a period of four hours between coating said adhesive onto a dental impress ion tray and adding said dental impression material.

9. In a process for preparing a dental impression by contacting teeth with a tray containing a curable dental impression material, the improvement comprising coating the tray with a dental adhesive prior to introducing impression material into the tray, said dental adhesive comprising, in weight percent based on the total weight of component (A) through (D) of the composition:
(A) from about 2% to about 20% of at least one organopolysiloxane rubber base;
(B) from about 10% to about 25% of at least one organopolysiloxane pressure sensitive adhesive;
(C) from about 30% to about 80% of at least one aliphatic unsaturation-functional organopolysiloxane M'Q resin;
(D) from about 1% to about 20% of at least one Si—H functional organopolysiloxane crosslinking agent containing minimally 3 Si—H bound hydrogens per molecule on average;
components (A) through (D) dissolved in
(E) sufficient organic solvent to obtain a solids content of ingredients (A) to (D) of from 30 percent to about 70% based on the total weight of the adhesive,
and wherein the sum of the weight percentages of components A to D is 100% based on the weight of components A to D.

10. The process of claim 9, wherein said organopolysiloxane rubber is a vinyl-functional organopolysiloxane rubber, and said $M^1Q$ resin (C) is a vinyl-functional MQ resin.

11. The process of claim 9, wherein said adhesive contains the components (A)–(D) in amounts of:
(A) 6%–10%
(B) 16%–22%
(C) 40%–70%
(D) 2%–10%.

12. The process of claim 9, wherein said adhesive exhibits substantial adhesion to both a curable organopolysiloxane dental impression material and a dental impression tray.

13. The process of claim 9, wherein said adhesive exhibits substantial adhesion to subsequently added dental impression material for a period of four hours between coating said adhesive onto a dental impression tray and adding said dental impression material.

14. The process of claim 9, wherein said organic solvent comprises an aliphatic hydrocarbon solvent.

15. The process of claim 9, wherein said adhesive is free of fillers having a mean particle size in excess of 10 μm.

16. The dental adhesive of claim 9, wherein said organic solvent is present in an amount of from 45–55 weight percent based on the sum of components (A) through (E).

17. An organopolysiloxane adhesive composition, comprising, in weight percent based on the total weight of component (A) through (D) of the composition:
(A) from about 2% to about 20% of at least one organopolysiloxane rubber base;
(B) from about 10% to about 25% of at least one organopolysiloxane pressure sensitive adhesive;
(C) from about 30% to about 80% of at least one aliphatic unsaturation-functional organopolysiloxane M'Q resin;
(D) from about 1% to about 20% of at least one Si—H functional organopolysiloxane crosslinking agent containing minimally 3 Si—H bound hydrogens per molecule on average;
components (A) through (D) dissolved in
(E) sufficient organic solvent to obtain a solids content of ingredients (A) to (D) of from 30 percent to about 70% based on the total weight of the adhesive;
wherein the sum of the weight percentages of components A to D is 100% based on the weight of components A to D, and wherein said adhesive composition contains no hydrosilylation catalyst.

18. The adhesive composition of claim 17, wherein said organopolysiloxane rubber is a vinyl-functional organopolysiloxane rubber, and said M'Q resin (C) is a vinyl-functional M'Q resin.

19. The adhesive composition of claim 17, containing the components (A)–(D) in amounts of:
(A) 6%–10%
(B) 16%–22%
(C) 40%–70%
(D) 2%–10%.

20. The adhesive of claim 17 which exhibits substantial adhesion to subsequently added dental impression material for a period of four hours between coating said adhesive onto a dental impression tray and adding said dental impression material.

* * * * *

UNITED STATES PATENT AND TRADEMARK OFFICE
CERTIFICATE OF CORRECTION

PATENT NO. : 6,251,966 B1  Page 1 of 1
DATED : June 26, 2001
INVENTOR(S) : Bryan E. Fry et al.

It is certified that error appears in the above-identified patent and that said Letters Patent is hereby corrected as shown below:

Column 10, claim 10,
Line 3, delete "$M^1Q$" and insert -- $M'Q$ --.

Signed and Sealed this

Nineteenth Day of February, 2002

Attest:

JAMES E. ROGAN
Attesting Officer  Director of the United States Patent and Trademark Office